United States Patent [19]

Watanabe et al.

[11] Patent Number: 4,988,505
[45] Date of Patent: Jan. 29, 1991

[54] DEODORIZER

[75] Inventors: Yoshitane Watanabe; Keitaro Suzuki; Mutsuko Suzuki; Eiji Okumura, all of Funabashi, Japan

[73] Assignee: Nissan Chemical Industries, Ltd., Tokyo, Japan

[21] Appl. No.: 404,674

[22] Filed: Sep. 8, 1989

[30] Foreign Application Priority Data

Sep. 16, 1988 [JP] Japan ................................ 63-232038
Apr. 11, 1989 [JP] Japan .................................. 1-91538

[51] Int. Cl.$^5$ .......................... A61L 9/04; A61L 9/00
[52] U.S. Cl. .................................. 424/76.3; 424/76.1; 252/309
[58] Field of Search ..................... 424/76.2, 76.4, 76.3; 252/303.1, 174.23, 309; 106/18.34

[56] References Cited

U.S. PATENT DOCUMENTS 4,753,753  6/1988  Kobashi et al. ...................... 252/309
4,770,812  9/1988  Watanabe et al. ................... 252/309
4,770,813  9/1988  Watanabe et al. ................... 252/309

OTHER PUBLICATIONS

Chemical Abstracts vol. 107: 136599z (1987).

Primary Examiner—Stanley J. Friedman
Assistant Examiner—Kevin E. Weddington
Attorney, Agent, or Firm—Frishauf, Holtz, Goodman & Woodward

[57] ABSTRACT

There is disclosed a deodorizer which comprises a colloidal antimony pentoxide. A surface of the colloidal antimony pentoxide may be modified by a metal compound, ammonia or an organic base and it may be further modified by an acidic substance.

The deodorizer of the present invention is effective to deodorize a basic gas such as ammonia, trimethylamine, triethylamine, etc.; an acidic gas such as hydrogen sulfide, acetic acid, butyric acid, isovaleric acid, methymercaptane, ethylmercaptane, methyl sulfide, methyl disulfide, etc.; an organic solvent gas such as tolunene, ethylacetate, methyl ethyl ketone, benzene acetaldehyde, etc.; and further to alleviate uncomfortable for example, odor causing gas daily generated such as nicotine smell, tar small, etc.

49 Claims, No Drawings

DEODORIZER

BACKGROUND OF THE INVENTION

This invention relates to a novel deodorizer which comprises colloidal antimony pentoxide and is capable of adsorbing and deodorizing various smell such as ammonia, amine, hydrogen sulfide, mercaptane, methyl sulfide, nicotine smell, etc.

At present, in a working surroundings of various industrial fields and in an usual living environment, odor causing gases such as ammonia, amine, hydrogen sulfide, mercaptane, methyl sulfide, ethyl acetate, toluene, isovaleric acid, aldehyde, etc. are generated, and these gases cause bad feelings as well as sometimes harming the human body. Thus, social interests concerning a method for removing an odor causing gas and findings a deodorizer for the some have been increased, and various deodorizers have actually been used for industrial and domestic uses.

As a deodorizer by an adsorbing method, various proposals have been made such as using an active charcoal, silica gel and titanium oxide-silica complex oxides (Japanese Provisional Patent Publication No. 137732/1988), titanium oxide-magnesia aggregate (Japanese Provisional Patent Publication No. 183065/1988), zeolite (Japanese Provisional Patent Publication No. 87852/1985), surface modified silica sol (Japanese Provisional Patent Publication No. 143069/1988), etc.

As the deodorizer, an activated charcoal (mainly coconut shell activated charcoal) has heretofore mainly been used, but the activated charcoal has a disadvantage that it has a small deodorizing effect to a basic gas such as ammonia, alkyl amine, etc., while it has deodorizing effects to mercaptan, hydrogen sulfide, benzene, etc. In order to overcome this disadvantage, a product in which an acid or an alkali, etc. is carried has been produced. However, since these acids and alkalis do not react with an activated charcoal, a product which to treat the above is required to be handled as in the acid or alkali, so that these are not preferred in practice. Also, the activated charcoal has disadvantages that it is difficult to mold, and, since it is black use forms are restricted.

Further, ammonia, an amine, etc. can be well deodorized by a material in which L-ascorbic acid is combined with iron sulfate, but the material has substantially no deodorizing effect to hydrogen sulfide, mercaptan and aldehyde, and also has a disadvantage that it cannot be used for deodorizing of a wet gas since it dissolves in water. In the case where the aforesaid iron sulfate and L-ascorbic acid are carried on a silica sol, the above disadvantage cannot be solved.

Colloidal silica (silica sol) has an extremely larger specific surface area and can adsorb ammonia in the presence of water. However, in a dried state, it has a small effect to adsorb an odor causing gas with itself and thus usually used as a carrier of deodorizing components in most cases.

While there has been reported that titanium oxide-magnesia aggregate is effective to deodorize various odor causing gas such as hydrogen sulfide, ammonia, amine, aldehyde, mercaptan, etc., there are disadvantages that it is high in cost and limited in use since it is powder.

As described above, the conventional deodorizers have disadvantages that kinds of odor causing gas capable of deodorizing or deodorizing effect are limited, use forms are limited or high in cost, etc.

SUMMARY OF THE INVENTION

The present inventors have intensively studied to overcome the above disadvantages and as the results, they have found that colloidal antimony pentoxide has good deodorizing effect on odor causing gases such as hydrogen sulfide, ammonia, amine, mercaptan, methyl sulfide, aldehyde, isovaleric acid, toluene, nicotine smell, etc. to accomplish the present invention.

An object of the present invention is to provide a novel deodorizer which has good deodorizing effects, is safe and easy in handling, and is capable of being used with various use forms.

That is, the present invention is a deodorizer which comprises colloidal antimony pentoxide.

DESCRIPTION OF THE PREFERRED EMBODIMENTS

Colloidal antimony pentoxide of the present invention is that having a primary particle diameter by an electron microscope observation of 2 to 200 m$\mu$, and preferably an acidic colloidal antimony pentoxide or a colloidal antimony pentoxide which a surface of the acidic colloidal antimony pentoxide is modified. As the surface-modified colloidal antimony pentoxide, there may be mentioned (1) a colloidal antimony pentoxide modified by a metal compound, (2) a colloidal antimony pentoxide modified by ammonia or an organic base, (3) a colloidal antimony pentoxide in which a surface of the above modified colloidal antimony pentoxide of (1) or (2) is further modified by an acidic substance, and (4) a colloidal antimony pentoxide in which a surface of a colloidal antimony pentoxide modified by a IV valence metal compound such as Ti, Zr and Sn is further modified by ammonia or an organic base.

These colloidal antimony pentoxides may be used singly or in combination of two or more.

In the following, the present invention will be described in more detail.

As the colloidal antimony pentoxide may be used those which are obtained by the conventionally known methods.

For example, as described in "Inorganic Colloid Chemistry", Vol. II, written by H. B. Weiser (1935), it can be obtained by hydrolysis of an antimony pentoxide aqueous solution or decomposition of a potassium pyrroantimonate aqueous solution by an acid, etc. Also, antimony pentoxide to be used in the present invention may be prepared by a method in which an alkali antimonate is heat treated at about 250° C. and then treated with a strong acid as described in Japanese Patent Publication No. 6695/1970, a method in which an antimony pentoxide gel formed by a reaction of sodium antimonate and an acid is dried as described in Japanese Provisional Patent Publication No. 250050/1985, a method in which an antimony pentoxide sol is formed from sodium antimonate or antimony trioxide, and the like.

In the present invention, the colloidal antimony pentoxide is preferably an acidic colloidal antimony pentoxide obtained by an acidic aqueous antimony pentoxide sol among the above methods of obtaining colloidal antimony pentoxide.

As a conventionally known method for obtaining an acidic aqueous antimony pentoxide sol, there have been known a method in which an alkali antimonate is dealkalized with an ion-exchange resin (U.S. Pat. No. 4,110,247), a method in which antimony trioxide is oxidized with hydrogen peroxide at a high temperature (Japanese Patent Publication No. 20479/1978), or a method in which sodium antimonate is reacted with an inorganic acid and then it is peptized with a phosphoric acid (Japanese Provisional Patent Publication No. 227918/1986).

In the method of oxidizing antimony trioxide by hydrogen peroxide, a hydrated antimony tetraoxide and a mixture of a hydrated antimony tetraoxide and a hydrated antimony pentaoxide can also be obtained as described in Japanese Provisional Patent Publication No. 21298/1977. In the present invention, these materials may possibly be used, but the hydrated antimony tetraoxide exhibits a yellow to orange color so that it is not necessarily preferred.

Further, in Japanese Provisional Patent Publication No. 125849/1987, an aqueous antimony sol obtained by antimony trioxide and hydrogen peroxide is described as hexaantimony tridecaoxide which is in an intermediate region between antimony pentoxide and antimony tetraoxide. This sol may be utilized as a colloidal antimony pentoxide of the present invention.

The aqueous sol obtained by the above method has a pH of 5 or lower. A primary particle diameter of a colloid of antimony pentoxide sol is usually 2 to 100 m$\mu$ by an electron microscopic observation, in the present invention, antimony pentoxide sol having a larger particle diameter in which a particle diameter exceeding 100 m$\mu$ to up to 200 m$\mu$ may also be used. It is difficult to obtain a sol having not more than 2 m$\mu$, and in a sol exceeding 200 m$\mu$, the effect is small and the production cost becomes expensive so that it is not preferred.

While a primary particle diameter of a colloidal antimony pentoxide, other than the sol, obtained by the above method in which the antimony pentoxide gel formed by the reaction of sodium antimonate and an acid is dried, etc. is not precise by an electron microscopic observation, it can be known by the BET method, etc. In each of the measuring methods, a primary particle diameter of a colloidal antimony pentoxide is as in the sol (2 to 200 m$\mu$).

The colloidal antimony pentoxide in the above antimony pentoxide sol can be represented by $Sb_2O_5\cdot(Na_2O)_x\cdot nH_2O$, and generally $X = 0$ to 0.4 and $n = 2$ to 4. This material agrees with peaks of $Sb_2O_5\cdot 4H_2O$ according to the X-ray diffractometry and thus it can be considered that it has a structure of $Sb_2O_5\cdot 4H_2O$.

When the above $Sb_2O_5\cdot(Na_2O)_x\cdot nH_2O$ is observed by the differential thermal analysis, a peak due to dehydration can be observed at 270° to 300° C. This dehydrated material shows peaks of anhydrous antimony pentoxide ($Sb_2O_5$) according to the X-ray diffractometry and no peak of sodium antimonate can be observed. An X-ray diffractometry pattern of $Sb_2O_5$ is substantially the same as $Sb_2O_5\cdot 4H_2O$ and the dehydrated material can be said as it is dehydrated while maintaining the structure of $Sb_2O_5\cdot 4H_2O$. While a dehydration mechanism of $Sb_2O_5\cdot nH_2O$ has not yet been clarified, there has been reported that complete dehydration is not carried out at the above temperature of 270° to 300° C. and water or -OH group (published by CRC Press, written by Abraham Clearfield, "Inorganic Ion Exchange Materials", (1982)). Also, there is a report that $Sb_3O_6OH$ is formed in the course of dehydration.

This dehydrated material has specific characteristics of becoming again to antimony pentoxide dehydrated material by absorbing water and being reversible on desorption of water. According to drying even at 200° C. or lower, water of crystallization often becomes n = 3 or less in $Sb_2O_5\cdot nH_2O$.

The antimony pentoxide sol to be used in the present invention is preferably those having an antimony pentoxide ($Sb_2O_5$) concentration of 2 to 40 % by weight.

A specific surface area by the BET method of a colloidal antimony pentoxide powder obtained by drying an antimony pentoxide sol or that obtained by the method other than the sol is 10 to 200 m$^2$/g in the antimony pentoxide hydrated material and 20 to 400 m$^2$/g in the antimony pentoxide after dehydration.

In Japanese Patent Publication No. 6695/1970, there is described that hydrated antimony pentoxide ($Sb_2O_5\cdot 4H_2O$) has good ion-exchangeability to an alkali metal ion, an alkaline earth metal ion, etc., and antimony pentoxide which is dehydrated, a hydrated antimony pentoxide under heating also has ion-exchangeability since it is the structure as $Sb_2O_5\cdot 4H_2O$.

Also, according to "Inorganic Chemistry" written by R. T. Sanderson (1967), there has been reported that antimony pentoxide ($Sb_2O_5$) is an amphoteric oxide and has stronger acidity than silica. It can be understood that antimony pentoxide is a solid acid since it shows a coloring of yellow by using 7,7,8,8-tetracyanoquinodimethane (TCNQ) which is the same as silica.

The colloidal antimony pentoxide of the present invention is extremely excellent in adsorbing and removing basic gases of ammonia or amines such as trimethylamine and triethylamine, etc. due to its characteristics such as inorganic ion exchange characteristics, acidity, solid acidity, high specific surface area, etc. Further, the colloidal antimony pentoxide of the present invention is also extremely excellent in removing nicotine smell. While in colloidal silica, the ability to remove nicotine smell is little, it can be considered that in the colloidal antimony pentoxide, cation exchangeability thereof is contributed to the removing effect.

Since the colloidal antimony pentoxide is an amphoteric oxide, it can adsorb an acidic gas, but it is strong in acidity; its deodorizing ability to acidic gases such as acetic acid, valeric acid or isovaleric acid is somewhat weak. Regrading deodorizing ability to gases of organic solvents such as toluene, ethyl acetate, methyl ethyl ketone, benzene, styrene, acetaldehyde, kerosine, gasoline, etc., it is somewhat weak when the above colloidal antimony pentoxide is used as it were. The present inventors have conducted investigations concerning modification of a surface of the colloidal antimony pentoxide, and they have found that the following modified colloidal antimony pentoxides of (1) to (4) are excellent in deodorizing effect as a deodorizer of an acidic gas or an organic solvent gas.

(1) A colloidal antimony pentoxide modified by a metal compound, preferably at least one metal compound selected from a metal of I valence, II valence, III valence and IV valence (provided that Ti, Zr and Sn only), which has a particularly excellent adsorbing and deodorizing effect to an acidic gas.

(2) A colloidal antimony pentoxide modified by ammonia or an organic base, which has a particularly excellent adsorbing and deodorizing effect to an organic solvent gas. As said organic base, there may preferably be mentioned at least one organic base selected from an amine, a quaternary ammonium salt and an amine type surfactant.

(3) A colloidal antimony pentoxide in which the above modified colloidal antimony pentoxide of (1) or (2) is partially modified by an acidic substance, which is further improved in adsorbing and deodorizing characteristics.

(4) A colloidal antimony pentoxide in which a surface of the colloidal antimony pentoxide modified by a IV valence metal compound (provided that Ti, Zr and Sn only) is further modified by ammonia or an organic base, which has an excellent adsorbing and deodorizing effect to an organic solvent gas as in (2).

The deodorizer of the above (1) which is excellent in adsorbing and deodorizing effect to an acidic gas can be obtained by adding, in an acidic antimony pentoxide sol, an aqueous solution or a solid of at least one metal compound selected from a metal of I valence, II valence, III valence and IV valence (provided that Ti, Zr and Sn only) and then stirring.

The deodorizer comprising the colloidal antimony pentoxide modified by the metal compound of (1) utilizes a cation exchangeability of the colloidal antimony pentoxide. The cation exchangeability of the colloidal antimony pentoxide is remarkably great and surprisingly, in case of sodium, it retains the structure of $Sb_2O_5 \cdot 4H_2O$ even when x in $Sb_2O_5 \cdot (Na_2O)_x \cdot nH_2O$ becomes 0.8 or more. In the case of a metal other than an alkali metal, the structure of $Sb_2O_5 \cdot 4H_2O$ is likewise maintained and does not take the structure corresponding to antimonate.

As the metal compound of I valence, II valence, III valence and IV valence (provided that Ti, Zr and Sn only) metals, hydroxides, oxides and salts are preferred. Specific examples of hydroxides, oxides and salts of said metals may include hydroxides such as $LiOH$, $NaOH$, $KOH$, $Mg(OH)_2$, $Ca(OH)_2$, $Sr(OH)_2$, $Ba(OH)_2$, $Zn(OH)_2$, $Sn(OH)_2$, $Ni(OH)_2$, etc.; oxides such as $MgO$, $CaO$, $SrO$, $BaO$, $ZnO$, $NiO$, etc.; salts such as $Li_2CO_3$, $Na_2CO_3$, $K_2CO_3$, $LiCl$, $NaCl$, $Li_2SO_4$, $Na_2SO_4$, $MgCl_2$, $CaCl_2$, $SrCl_2$, $BaCl_2$, $Mg(NO)_3$, $Ca(NO)_3$, $Mg(OH)_3 \cdot 3MgCO_3$, $CaCO_3$, $MgCO_3$, $MgSO_4$, $ZnCl_2$, $ZnSO_4$, $ZnCO_3$, $Pb(OH)_2$, $PbCO_3$, $Pb(NO_3)_2$, $Sn(OH)_2$, $SnCO_2$, $FeCl_2$, $FeSO_4$, $NiSO_4$, $CuSO_4$, $CuCl_2$, $Al_2(OH)_5Cl$, $Al_2SO_4$, $Al(NO_3)_3$, sodium aluminate, $Cr(NO)_3$, $BiOCl$, $KAl(SO_4)_2 \cdot 12H_2O$, $SbOCl$, $ZrOCl_2$, $ZrO(NO_3)_2$, zirconyl carbonate, $K_3SnO_3 \cdot 3H_2O$, $TiCl_4$, $SnCl_4$, etc.

It is preferred that a water-soluble hydroxide or salt is dissolved in water and then added to an acidic antimony pentoxide sol. In this case, the aforesaid metal cation is strongly adsorbed and bonded to a cation exchange cite of the antimony pentoxide hydrate.

An amount to be added of the above metal compound is, in terms of oxide, 0.1 to 40 % by weight based on $Sb_2O_5$. If it is less than 0.1 % by weight, added the effect is small, while it exceeds 40 % by weight, the acidic property of the antimony pentoxide becomes small so that it is not preferred.

In the present invention, when oxides, hydroxides, carbonates, etc., which have less solubility to water, are added, these compounds are strongly adsorbed on the surface of the antimony pentoxide colloid. It can be estimated that surface modification of the colloidal antimony pentoxide can be carried out by the reason that the antimony pentoxide is a strong acid whereby it forms soluble salts with the aforesaid oxides, hydroxides, carbonates, etc., and is dissolved in a small amount of an acid (hydrochloric acid, sulfuric acid, etc.) existing in the sol so that formed cations are incorporated into the colloidal antimony pentoxide and thus dissolution of oxides, hydroxides, carbonates, etc. is promoted.

When the metal salts are used, partial deanionization by an anion exchange resin, or due to the ultrafiltration method or the centrifugal filtration and washing is required. If an anion is present with a large amount, it causes a problem of corrosion, etc., and sometimes a lower deodorizing effect so that it is not preferred.

A pH of the colloidal antimony pentoxide sol or a slurry modified by the above metal compound becomes 1 to 11. The deodorizing effects are the same even when it exceeds 11, but basicity is too strong whereby it is not preferred in handling.

Metal ions exceeding cation exchangeability become hydroxides or oxides by drying and attach on the surface of the colloidal antimony pentoxide. Coloring by the above TCNQ is yellowish with a portion of less metal ion, which shows properties of a solid acid of $Sb_2O_5$ remaining. By making an added amount of the metal ion larger, coloring changes and both properties of a solid, acid and a solid base reveal. An acid-base balance can be controlled by selecting kinds and amounts of metals to be added in the present invention, and thus, an adsorption balance of a basic gas-acidic gas can be controlled.

The deodorizer comprising the modified colloidal antimony pentoxide of the above (2) which is excellent in adsorbing and deodorizing effect to a gas of an organic solvent can be obtained by adding, in an acidic antimony pentoxide sol, at least one compound selected from ammonia and an organic base, preferably an organic basic compound such as an amine, a quaternary ammonium hydroxide and an amine type surfactant.

As the amine, there may be mentioned monoethanol amine, triethanol amine, N-(α-aminomethyl)ethanolamine, etc. As the quaternary ammonium salt, there may be mentioned tetraethanolammonium hydroxide, monomethyltriethanolammonium hydroxide, etc. As the amine type surfactant, there may be mentioned alkylamine oxidized ethylene derivatives having ethylene oxide added moles of 1 to 30 such as polyoxyethylenedodecylamine, polyoxyethyleneoctadecylamine, polyoxyethylene tallow alkylamine, polyoxyethylene tallow alkylpropylenediamine, etc. Among these, the amine type surfactant is preferred since the lipophilic property can be controlled by added moles of ethylene oxide. By controlling this lipophilic property, kinds of an organic solvent gas can be selected.

These organic bases or ammonia are strongly adsorbed at a cation exchange cite of the colloidal antimony pentoxide, so that these have properties that the specific surface area of the colloidal antimony pentoxide can be utilized effectively, deodorizing and adsorbing ability to an organic solvent gas can be improved and the organic base which is a modifier is hardly dissolved or flew out by water, etc.

As the organic base, a quaternary ammonium salt, an amine salt and a cationic surfactant may be used in addition to the above, but they are not necessarily preferred since an amount of anion becomes large so that the anion should be removed by anoin exchange, filtration and washing, etc.

In the present invention, an amount added of the above ammonia and the organic base is preferably 0.05 to 50 % by weight based on antimony pentoxide ($Sb_2O_5$). If it is less than 0.05 % by weight the modifying effect is small, while if it exceeds 50 % by weight, the added effect reveals, the material becomes sticky whereby handling becomes trouble-some so that it is not preferred.

The above deodorizer (3) is to improve-deodorizing effect by further adding an acidic substance to the modified colloidal antimony pentoxide of the above (1) or (2).

As the acidic substance, there may preferably include an organic acid such as oxalic acid, tartaric acid, citric acid, stearic acid, L-ascorbic acid, alkylbenzenesulfonic acid, paratoluenesulfonic acid, etc.; glyoxal; and an inorganic acid such as silicic acid, phosphoric acid, metaphosphoric acid, pyrophosphoric acid, sulfuric acid, molybdic acid, tungstic acid, vanadic acid, etc.

An amount of the above acidic substance to be added is preferably 0.05 to 20 % by weight based on antimony pentoxide ($Sb_2O_5$) If it is less than 0.05 % by weight, the modifying effect is small, while if it exceeds 20 % by weight, the acid is too much and a characteristic of a base is lost so that it is not preferred.

The deodorizer comprising a modified colloidal antimony pentoxide which is excellent in adsorbing and deodorizing effect to an organic solvent gas of the above (4) can be obtained by modifying a surface of a colloidal antimony pentoxide with a IV valence metal compound (provided that Ti, Zr and Sn only) among the metal compound described in the above (1) in the same manner as in (1), and further modifying it with ammonia or an organic base used in the above (3). An amount of ammonia or an organic base to be used at this time is preferably 0.05 to 50 % based on antimony pentoxide ($Sb_2O_5$).

While the above modified colloidal antimony pentoxides of (1) to (4) can be obtained by adding the above modifier to the acidic antimony pentoxide sol, a temperature at which the modifier is added is preferably room temperature to 150 °C. It is possible at a temperature in excess of 150° C., but the production cost increases so that it is not preferred. After addition, it becomes a sol or a slurry. In the case where it is a slurry containing much amount of anions such as metal salts, etc., it is preferred to use it after removing anions by filtration and washing, and then the resulting cake is redispersed in water to make a slurry.

As a form of the deodorizer comprising a colloidal antimony pentoxide of the present invention, powder may be mentioned. As a method for obtaining said powder, there may be mentioned a method in which the above acidic antimony pentoxide sol, the modified antimony pentoxide sol or the modified slurry is dried by a spray drier, drum drier, lyophilization, hot-air drying, etc., and then pulverized with a dry type pulverizer such as a Jet-O-Mizer, a pin disc mill, a mixer, a ball mill, etc., depending on necessity.

In the present invention, powder comprising an acidic antimony pentoxide sol or a colloidal antimony pentoxide obtained by a modified antimony pentoxide sol or slurry may be used as a deodorizer singly or in combination. A specific surface area of the resulting powder is 10 to 400 $m^2/g$.

Those which are dried at a drying temperature of 250 °C. or lower are colloidal antimony pentoxide hydrates and those obtained at a drying temperature exceeding about 250 °C. are anhydrides containing less amount of water of crystallization by dehydration. Each of which may be used as a deodorizer. Drying of the colloidal antimony pentoxide modified by an organic substance such as an amine should be carried out at a temperature range not generating decomposition of the organic substance. Also, if the colloidal antimony pentoxide obtained by the acidic sol is dehydrated, it shows a pale yellow to yellow color, those surface modified by an alkali metal, an alkaline earth metal, etc. show white to pale yellow color even when they are anhydride. Structures after heating at 300 °C. or higher are not so changed from those before heating. However, if the heating temperature exceeds 600 °C., they react to form antimonate (for example, sodium antimonate), whereby the structure of the antimony pentoxide is lost an the adsorbing effect is lowered so that it is not preferred.

The sol or slurry comprising the colloidal antimony pentoxide of the precent invention can adsorb or deodorize water soluble odor causing gases by using it as a deodorizer in the form of a liquid.

Also, since the deodorizer comprising the colloidal antimony pentoxide of the present invention can be used, as mentioned above, by drying a sol or slurry as they were, deodorizes comprising the colloidal antimony pentoxide with various forms can be extremely easily prepared by a method in which the acidic antimony pentoxide sol, surface-modified antimony pentoxide sol or slurry is impregnated in or coated on a porous molded material or a sheet such as a paper, a fiber, a fabric, a non-woven fabric, a glass wool, a ceramic fiber, a ceramic, a wood chip, a plastics, a metal, etc., and then dried.

Also, in the case of a paper, the above antimony pentoxide sol or slurry can be introduced during making paper, while in the case of a fiber, a fiber containing a deodorizer can be obtained by adding a larger amount of a sol to a spinning raw material (dope) at spinning.

Further, a deodorizing ability can be applied to a molded material such as a paper, a plastic, a ceramic, etc. by a method in which a resin emulsion and the above antimony pentoxide sol or slurry are mixed, coated on these materials and dried.

In the deodorizer comprising the colloidal antimony pentoxide of the present invention, in the case of powder, it may be used by putting in a breathable bag in the same manner as in the conventionally known deodorizing powder. Further, the above various forms of deodorizers can be prepared by a method in which water and if necessary a molding aid are added to the deodorizing powder of the present invention, and after molding it to a desired shape such as a granular, tablet, sphere, cylinder, plate, rod, film, honeycomb, ribbon, etc. by a conventionally known granulating method or molding method such as a pressure molding, extrusion molding, tumbling granulator, etc. and then drying at a room temperature to 600 °C.

In the present invention, various surfactants, extenders, binders, etc. may combinedly be used so long as they do not impair a deodorizing effect.

Also, by mixing powder during plastic molding, a plastic film, sheet, or vessel containing a deodorizer can be prepared.

Since the deodorizer of the present invention comprises only inorganic substances except for those modified by an organic substance such as an amine, etc., it has good heat resistance and can be used again by after desorbing an adsorbed odor causing by heating.

The deodorizer comprising the colloidal antimony pentoxide of the present invention is effective to deodorize a basic gas such as ammonia, trimethylamine, triethylamine, etc.; an acidic gas such as hydrogen sulfide, acetic acid, butyric acid, isovaleric acid, methyl-mercaptane, ethylmercaptane, methyl sulfide, methyl disulfide, etc.; an organic solvent gas such as toluene, ethyl acetate, methyl ethyl ketone, benzene, actaldehyde, etc.; and further to alleviate uncomfortable odors, e.g., odors daily generated such as nicotine smell, tar smell, etc.

Since the deodorizer of the present invention can be used by drying an acidic antimony pentoxide sol, a modified antimony pentoxide sol or a modified slurry as it were, a deodorant molding product which is good in efficiency can be obtained by easily impregnating in or coating on a paper, a fiber, an inorganic fiber, a sheet or a porous molded product of a ceramic, etc. Also,, the deodorant power of the present invention is easily molded and can be added to plastics, etc. The deodorizer comprising the colloidal antimony pentoxide of the present invention can be converted into various forms of deodorizers as mentioned above.

The deodorizer of the present invention can be used for a extremely wide range of uses as industrial and domestic deodorizers, for example, to deodorize smell gases, solvent gases, etc. generated in chemical factories, resin processing factories, paint or adhesive factories, paper manufacturing factories, sewage disposal factories, industrial waste disposal factories, organic fertilizer factories, food factories, etc.; to deodorize cattle sheds, pigpens, pets, sewage purification tanks, toilets, garbages, etc.; and to deodorize nicotine smell in automobiles, indoors, etc., sanitary items, paper diapers, pads inside of shoes, etc.

EXAMPLES

Next, the present invention will be described in more detail by referring to Examples, but the present invention is not limited by these Examples.

In Examples, all "%" mean "% by weight".

EXAMPLE 1

In 2 liters of a reaction apparatus made of a glass was charged 200 g of sodium antimonate (64 % of $Sb_2O_5$, 12 5 % of $Na_2O$ and 23.5 % of $H_2O$ ), and it was dispersed by adding 500 g of water and then 190 g of a 35 % hydrochloric acid was added thereto while stirring to react the mixture at 30° C. for 3 hours. A concentration of antimony pentoxide in the reaction mixture was 14.4 % in terms of $Sb_2O_5$. Then, an antimony pentoxide gel slurry formed from the reaction mixture was subjected to suction filtration and 1200 g of a 3.6 % hydrochloric acid aqueous solution was injected to remove sodium ion in the antimony pentoxide gel. Further, it was washed with 2400 g of water to remove remaining hydrochloric acid. In 2 liters of a reaction apparatus made of a glass was charged 210 g of a wet cake of the resulting antimony pentoxide, it was dispersed by adding 640 g of water and after 3.6 g of a 85 % phosphoric acid was added thereto while stirring, the mixture was heated to 85° C. to peptize for one hour. The resulting antimony pentoxide sol had a specific gravity of 1.172, a pH of 1.90, a viscosity of 4.5 cp, $Sb_2O_5$ of 16.4%, $Na_2O$ of 0.024 %, Cl of 120 ppm and a particle diameter of 15 to 25 m$\mu$ (observation by electron microscope, hereinafter referred to as "electron microscope particle diameter").

This acidic antimony pentoxide sol was dried by a spray drier (product temperature of 130° C.) to obtain deodorizer white powder of the colloidal antimony pentoxide.

An average particle diameter of the deodorizer powder was 13.5 $\mu$ and a specific surface area by the BET method was 92 m$^2$/g.

As a result of powder X-ray diffractometry, it had a $Sb_2O_5.4H_2O$ structure and as a result of differential thermal analysis, water of crystallization was about 15 % by weight. A sintered product of the powder sintered at 350° C. (an amount of water of crystallization of 3 %) had a pale yellow color and a specific surface area by the BET method of 110 m$^2$/g.

EXAMPLE 2

In 3 liters of a reaction apparatus made of a glass was charged 200 g of sodium antimonate which was the same as used in Example 1, it was dispersed by adding 600 g of water and then excessive amounts (1200 ml) of cation exchange resin (produced by Tokyo Yuki Kagaku Kogyo, trade name: Amberlite 120B), and the mixture was stirred at 35° C. to give an acidic antimony pentoxide sol. The resulting acidic antimony pentoxide sol had a specific gravity of 1.128, a pH of 2.13, a viscosity of 2.4 cp, $Sb_2O_5$ of 10.4 %, $Na_2O$ of 0.62 %, $Na_2O/Sb_2O_5$ molar ratio of 0.31 and an electron microscope particle diameter of 20 to 40 m$\mu$.

A specific surface area by the BET method of a material dried the sol at 120° C. was 72.2 m$^2$/g. A specific surface area by the BET method of a material dried at 300° C. was 120 m$^2$/g.

To 1200 g of this sol was added 98 g of $Ba(OH)_2 8H_2O$ and the mixture was stirred at room temperature for 30 minutes and then elevated to 80° C. and stirred for about 2 hours. The resulting liquor was substantially sol state while modified antimony pentoxide colloids were micro-agglomerated and had a pH of 10.2.

After this liquor was dried by a hot-air dryer at 150° C., it was pulverized by a pin disc mill to give a deodorizer white powder of surface-modified colloidal antimony pentoxide. A $(Na_2O+BaO)/Sb_2O_5$ molar ratio of this powder was 1.1.

An average particle diameter of the deodorizer powder was 3.8 $\mu$ and a specific surface area by the BET method was 76 m$^2$/g. Also, a sintered product of the powder sintered at 350° C. had a slightly yellowish white color and a specific surface area by the BET method of 120 m$^2$/g.

EXAMPLE 3

In 2 liters of a reaction apparatus made of a glass was charged 300 g of sodium antimonate which was the same as used in Example 1, it was dispersed by adding 310 g of water and then 160 g of a 35 % hydrochloric acid was added while stirring, and the mixture was reacted at 25° C. for 3 hours. Then, an antimony pentoxide gel slurry formed from the reaction mixture was subjected to suction filtration and washed with 5000 g of water to give 340 g of an antimony pentoxide wet cake. In 2 liters of an apparatus was charged this wet cake, 240 g of water was added thereto and then 3.0 g of a 85 % phosphoric acid and 19 g of triethanol amine were added thereto, and the mixture was heated at 85° C. for 2 hours to give antimony pentoxide sol. The resulting antimony pentoxide sol had a specific gravity of 1.443, a pH of 6.61, a viscosity of 4.3 cp, $Sb_2O_5$ of 32.6 %, $Na_2O$ of 2.06 %, $Na_2O/Sb_2O_5$ molar ratio of 0.33 and an electron microscope particle diameter of 5 to 15 m$\mu$.

This sol was diluted with water to a $Sb_2O_5$ concentration of 13.0 % and it was passed through a column filled with a cation exchange resin to give an acidic antimony pentoxide sol.

The resulting antimony pentoxide sol had a specific gravity of 1.140, a pH of 1.98, a viscosity of 3.8 cp, $Sb_2O_5$ of 13.0 %, $Na_2O$ of 0.72 %, $Na_2O/Sb_2O_5$ molar ratio of 0.29, Cl of 180 ppm, an amine of 0 % and an electron microscope particle diameter of 5 to 15 m$\mu$.

A specific surface area by the BET method of a material dried the sol at 130 °C. was 154 m$^2$/g. A specific surface area by the BET method of a material dried at 350 °C. was 292 m$^2$/g.

To 1310 g of this sol was added 35 g of calcium hydroxide and the mixture was stirred at room temperature for one hour and then stirred at 80 °C. for 3 hours. The resulting liquor was a high viscosity slurry and had a $(Na_2O + CaO)/Sb_2O_5$ molar ratio of 1.2.

After this liquor was dried by a hot-air dryer at 150 °C., it was pulverized by a pin disc mill to give a deodorizer white powder of surface-modified colloidal antimony pentoxide. An average particle diameter of the powder was 4.2 $\mu$ and a specific surface area by the BET method was 140 m$^2$/g.

EXAMPLE 4

To 1000 g of the acidic antimony pentoxide sol obtained in Example 1 was added 6.6 g of polyoxyethylenedodecylamine having an average added mole number of ethylene oxide of 7, and the mixture was stirred at room temperature for 30 minutes. This liquor was a sol having a pH of 2.2.

This sol was dried by a spray drier (product temperature of 120 °C.) to give a white powder deodorizer of surface-modified colloidal antimony pentoxide. An average particle diameter of the resulting powder was 16.2 $\mu$ and an amount of polyoxyethylenedodecylamine was 4 % by weight based on $Sb_2O_5$.

EXAMPLE 5

To 1000 g of the acidic antimony pentoxide sol obtained in Example 1 was added 33 g of polyoxyethylene tallow alkylamine having an average added mole number of ethylene oxide of 2, and the mixture was stirred at room temperature for 30 minutes. This liquor was a slurry of hydrophobic agglomerates comprising colloidal antimony pentoxide and polyoxyethylene tallow alkylamine, and having a pH of 6.8. After this slurry was dried by a hot-air drier at 110 °C., it was pulverized by a pin disc mill to give a white powder deodorizer of surface-modified colloidal antimony pentoxide. An average particle diameter of the resulting powder was 5.2 $\mu$ and an amount of polyoxyethylene tallow alkylamine was 20 % by weight based on $Sb_2O_5$.

EXAMPLE 6

To 960 g of the acidic antimony pentoxide sol prepared in Example 3 was added 78 g of $Ba(OH)_2 \cdot 8H_2O$, and the mixture was stirred at room temperature for 30 minutes, and then at 80 °C. for 2 hours. After cooling, 10 g of tartaric acid was added to the mixture and the mixture was stirred for 30 minutes. The resulting liquor was a sol state having a pH of 7.5. After this liquor was dried by a hot-air drier at 130 °C., it was pulverized by a pin disc mill to give a white powder deodorizer of surface-modified colloidal antimony pentoxide. An average particle diameter of the resulting powder was 3.8 $\mu$, a $(Na_2O+BaO)/Sb_2O_5$ molar ratio was 0.95 and an amount of tartaric acid was 8 % by weight based on $Sb_2O_5$.

EXAMPLE 7

In 1500 g of water was dispersed 720 g of sodium antimonate which was the same as that used in Example 1, and the reaction was carried out at 20 °C. for 2 hours while adding 610 g of a 35 % hydrochloric acid. After completion of the reaction, the mixture was subjected to suction filtration, and washed with water by using 6000 g of water. The resulting cake was dried by a hot-air dryer at 150 °C. and pulverized by a pin disc mill. As a result of X-ray diffractometry of the resulting deodorizer white powder, it had a $Sb_2O_5 \cdot 4H_2O$ structure and had an average particle diameter of 7 $\mu$ and a $Na_2O/Sb_2O_5$ molar ratio of 0.32. This material was agglomerates of colloidal antimony pentoxide and a specific surface area by the BET method of 12 m$^2$/g.

A particle size from the specific surface area was 140 m$\mu$ and a primary particle size by an electron microscope was 100 to 200 m$\mu$.

EXAMPLE 8

By using 200 g of sodium antimonate (64 % of $Sb_2O_5$, 12.5 % of $Na_2O$ and 23.5 % of $H_2O$), a wet cake of antimony pentoxide was obtained in the same manner as in Example 1. In 2 liters of a reaction apparatus made of a glass was charged 210 g of this wet cake, it was dispersed by adding 730 g of water and after 7.3 g of a 85 % phosphoric acid was added thereto while stirring, the mixture was heated to 85 °C. to peptize for one hour. The resulting antimony pentoxide sol had a specific gravity of 1.140, a pH of 1.78, a viscosity of 4.5 cp, $Sb_2O_5$ of 13.5 %, $Na_2O$ of 0.021 %, Cl of 100 ppm and an electron microscope particle diameter of 5 to 10 m$\mu$.

This acidic antimony pentoxide sol was dried by a spray drier (product temperature of 130 °C.) to obtain deodorizer white powder of the colloidal antimony pentoxide.

An average particle diameter of the deodorizer powder was 13.5 $\mu$ and a specific surface area by the BET method was 120 m$^2$/g.

As a result of powder X-ray diffractometry, it had a $Sb_2O_5 \cdot 4H_2O$ structure and as a result of differential thermal analysis, water of crystallization was about 15 % by weight.

EXAMPLE 9

To 2000 g of the acidic antimony pentoxide sol (13.5 % of $Sb_2O_5$, electron microscope particle diameter of 5 to 10 m$\mu$) obtained in the same manner as in Example 8 was added 135 g of zirconyl carbonate (produced by Diichikigenso Kagaku K.K., 40 % in terms of $ZrO_2$), and the mixture was stirred at 90 °C. for one hour to give zirconia-modified antimony pentoxide slurry. This slurry had a $ZrO2/Sb_2O_5$ molar ratio of 0.53 and a pH of 1.80.

After this slurry was dried by a hot-air drier at 150 °C., it was pulverized by a pin disc mill to give a white powder deodorizer of surface-modified colloidal antimony pentoxide. An average particle diameter of the resulting powder was 5.0 $\mu$.

EXAMPLE 10

To 2000 g of the acidic antimony pentoxide sol (13.5 % of $Sb_2O_5$, electron microscope particle diameter of 5 to 10 m$\mu$) obtained in the same manner as in Example 8 was added 128.6 g of zirconyl carbonate (produced by Diichikigenso Kagaku K.K., 40 % in terms of $ZrO_2$), and the mixture was stirred at 90 °C. for one hour and then 80 g of a 28 % aqueous ammonia was added thereto followed by stirring for 30 minutes to give zirconia ammonia-modified antimony pentoxide slurry. This slurry had a $ZrO_2/Sb_2O_5$ molar ratio of 0.5, a $(NH_4)_2O/Sb_2O_5$ molar ratio of 0.79 and a pH of 10.

After this slurry was dried by a hot-air drier at 150° C., it was pulverized by a pin disc mill to give a white powder deodorizer of surface-modified colloidal antimony pentoxide. An average particle diameter of the resulting powder was 4.5 $\mu$ and a pH of a 10 % water dispersion of this powder was 9.29.

EXAMPLE 11

To 2000 g of the acidic antimony pentoxide sol (13.5 % of $Sb_2O_5$, electron microscope particle diameter of 5 to 10 m$\mu$) obtained in the same manner as in Example 8 was added 86.1 g of a 28 % aqueous ammonia followed by stirring for 30 minutes to give ammonia-modified antimony pentoxide slurry. This slurry had a $(NH_2)_2O/Sb_2O_5$ molar ratio of 0.85 and a pH of 10.2.

This slurry was dried by a spray drier (product temperature of 130° C.) to give a white powder deodorizer of surface-modified colloidal antimony pentoxide. An average 7 35 particle diameter of the resulting powder was 1.5 $\mu$ and a pH of a 10 % water dispersion of this powder was 8.2.

COMPARATIVE EXAMPLE 1

To 1000 g of the acidic antimony pentoxide sol obtained in the same manner as in Example 2 was gradually added 52 g of a solid NaOH (93 % purity) and the mixture was stirred for one hour. The resulting liquor was a sol having a pH of 14 or higher. While this sol was dried by a hot-air drier, the dried material showed deliquescent phenomenon since the surface thereof was NaOH so that it was difficult to use as a deodorizer.

COMPARATIVE EXAMPLE 2

An acidic aqueous silica sol (produced by Nissan Chemical Industries, Ltd., trade name: Snowtex-O 20 % of $SiO_2$, a pH of 2.7 and a particle diameter of 10 to 20 m$\mu$) was dried by a spray drier to give silica powder. The resulting silica powder had an average particle diameter of 8.5 $\mu$ and a specific surface area by the BET method of 209 m²/g.

(Evaluation of deodorizers)
Evaluation method 1

In a culture dish was charged 5 g of a deodorizer powder obtained in Examples, and it was allowed to stand overnight in a desiccator with a culture dish charged with an aqueous ammonia or n-propylamine, and the deodorizer was taken out. Then, amounts of ammonia and propylamine adsorbed to the deodorizer were measured by an elemental analysis. For comparison, the same evaluation was carried out with respect to powder obtained in Comparative example 2. The results are shown in Table 1.

TABLE 1

|  | Adsorbed amount (Note 3) (% by weight) | |
|---|---|---|
|  | Ammonia | Propylamine |
| Example 1 (Note 1) | 5.12 | 2.60 |
| Example 1 (Note 2) | 4.96 | 2.46 |
| Example 4 | 3.54 | 1.89 |
| Example 7 | 2.81 | 1.48 |
| Comparative | 0.5 or less | 0.2 or less |

TABLE 1-continued

|  | Adsorbed amount (Note 3) (% by weight) | |
|---|---|---|
|  | Ammonia | Propylamine |
| example 2 |  |  |

(Note 1) Powder dried at 130° C.
(Note 2) Powder dried at 350° C.
(Note 3) An amount based on the deodorizer.

Evaluation method 2

In a culture dish was charged 5 g of a deodorizer powder obtained in Examples, and it was allowed to stand overnight in a desiccator with a culture dish charged with acetic acid or an ethanol solution of ethylmercaptane, or an apparatus generating hydrogen sulfide by adding diluted hydrochloric acid to iron sulfide, and the deodorizer was taken out. Then, amounts of acetic acid and ethylmercaptane adsorbed to the deodorizer were measured by an elemental analysis and that of hydrogen sulfide by a fluorescent X-ray analysis. For comparison, the same evaluation was carried out with respect to powder obtained in Comparative example 2. The results are shown in Table 2.

TABLE 2

|  | Adsorbed amount (% by weight) (Note 1) | | |
|---|---|---|---|
|  | Acetic acid | Hydrogen sulfide | Ethylmercaptane |
| Example 2 | 8.3 | 2.8 | 2.3 |
| Example 3 | 10.4 | 4.0 | 3.8 |
| Example 4 | 2.1 | 0.8 | 0.6 |
| Example 6 | 6.8 | 2.1 | 2.0 |
| Comparative example 2 | Each of them cannot be measured since adsorbed amount was too little. | | |

(Note 1) An amount based on the deodorizer.

Evaluation method 3 (adsorption test to nicotine smell)

To a corrugated cardboard paper were impregnated the antimony pentoxide sol or modified antimony pentoxide sol obtained in Examples 1, 2 and 4 which was made deodorizer powder by drying and the silica sol in Comparative example 2 for comparative purposes, respectively, and the materials were dried at 105° C. to prepare filter-like deodorizers. This filter-like deodorizer was attached to a glass tube and smoke generated from 5 pieces of cigarettes were introduced therein by an air pump.

After sending smoke of cigarettes, the filter was taken off and a physical function test was carried out. As the results, in the filters of Examples 1, 2 and 4, a nicotine smell was strongly felt, respectively, whereas in the filter of Comparative example 2, substantially no smell was felt.

When these filters were charged in a bag made of polyethylene and allowed to stand day and night, no nicotine smell was felt.

Evaluation method 4 (Adsorption test of organic solvent smell)

The deodorizer powder of Examples 4, 5 and 6 and powder of Comparative example 2 were each charged in a culture dish, and these culture dishes were charged in a desiccator. Then, toluene and methyl acrylate monomer gases were discharged therein and a deodorizing effect after one hour was examined by a physical function test. As the results, in the cases of Examples 4, 5 and 6, deodorizing effects can clearly be admitted. Particularly, Example 5 shows extremely good results. In Comparative example 2, no deodorizing effect can be admitted.

Evaluation method 5

A L-shaped glass tube and one liter of an Erlenmeyer flask equipped with a bad smelling substance injecting hole by using a syringe and a ground stopper made of a glass in which a glass tube equipped with a stopper made of silicone rubber was perpendicularly and slightly sticking out at an upper portion thereof, which was used as a sampling hole for analysis were prepared. One end of the L-shaped glass tube was sticking out by an upper portion of the Erlenmeyer flask and a bag of non-woven fabric charged with 1 g of a deodorizer therein was hung with a string at this portion. To another end of the glass tube was attached a packing having a small hole. At the bottom of the Erlenmeyer flask, a magnet stirrer bar was placed to carry out stirring by a stirrer.

By using this apparatus and also using deodorizers shown in Tables 3 to 7, bad smelling substances were added with a predetermined amount with a syringe, and immediately thereafter, a concentration was measured by a gas chromatography or an indicator tube by sampling with a syringe.

A concentration immediately after injection of the bad smelling substance was made with an initial concentration. Thereafter, a sampling was effected by a syringe with each of predetermined time, and a remaining ratio of the bad smelling substance was measured by analysis. The results are also shown in Tables 3 to 7.

Comparative examples 3 and 4

By using an active charcoal used in a commercially available deodorizer (a deodorizer for refrigerator produced by Hakugen K.K. trade name: Nonsmell), measurements were carried out according to the above evaluation method 5 with respect to ammonia and ethylmercaptane. The results are shown in Table 3 and Table 5, respectively.

TABLE 3

| Bad smell substance Deodorizer | Ammonia | | | |
|---|---|---|---|---|
| | Example 8 | | Comparative example 3 | |
| Time (min) | ppm | Remaining ratio | ppm | Remaining ratio |
| 0 | 4400 | 100% | 3000 | 100% |
| 5 | 2600 | 59.1 | 2900 | 97.0 |
| 10 | 800 | 18.2 | 2100 | 70.0 |
| 20 | 400 | 9.1 | 1600 | 53.0 |
| 30 | 22 | 0.5 | 1300 | 43.0 |
| 40 | 9.5 | 0.2 | 1200 | 40.0 |
| 60 | 8.0 | 0.2 | 1160 | 39.0 |
| 90 | 5.0 | 0.1 | — | — |

As shown in Table 3, the deodorizer of the present invention shows a superior deodorizing effect to the active charcoal.

TABLE 4

| Bad smell substance Deodorizer | Trimethylamine Example 8 | | Hydrogen sulfide Example 8 | |
|---|---|---|---|---|
| Time (min) | ppm | Remaining ratio | ppm | Remaining ratio |
| 0 | 3981 | 100% | 1763 | 100% |
| 5 | 2745 | 69.0 | 44 | 2.5 |
| 10 | 2008 | 50.4 | 0.03 | 0.01 |
| 20 | 989 | 24.8 | — | — |
| 30 | 776 | 19.5 | — | — |
| 40 | 653 | 16.4 | — | — |

TABLE 4-continued

| Bad smell substance Deodorizer | Trimethylamine Example 8 | | Hydrogen sulfide Example 8 | |
|---|---|---|---|---|
| Time (min) | ppm | Remaining ratio | ppm | Remaining ratio |
| 60 | 398 | 10.0 | — | — |
| 90 | 139 | 3.5 | — | — |

TABLE 5

| Bad smell substance Deodorizer | Ethylmercaptane | | | |
|---|---|---|---|---|
| | Example 9 | | Comparative example 3 | |
| Time (min) | ppm | Remaining ratio | ppm | Remaining ratio |
| 0 | 4218 | 100% | 3223 | 100% |
| 5 | 1549 | 36.7 | 1520 | 47.2 |
| 10 | 525 | 12.4 | 388 | 12.0 |
| 15 | 201 | 4.8 | 297 | 9.2 |
| 20 | 69 | 1.6 | 193 | 6.0 |
| 30 | 12 | 0.3 | 96 | 3.0 |
| 40 | 7 | 0.2 | — | — |
| 60 | — | — | 36 | 1.1 |
| 90 | — | — | 14 | 0.4 |

From the results in Table 5, it can be understood that the sample of the comparative example is slow in adsorbing rate and a bad small cannot be removed easily since 1.1 % of ethylmercaptane remains even after 60 minutes whereas that of the present invention is 0.2 % after 40 minutes.

TABLE 6

| Bad smell substance Deodorizer | Acetaldehyde | | | |
|---|---|---|---|---|
| | Example 10 | | Example 11 | |
| Time (min) | ppm | Remaining ratio | ppm | Remaining ratio |
| 0 | 4925 | 100% | 5000 | 100% |
| 5 | 2603 | 52.9 | 3115 | 62.3 |
| 10 | 1540 | 31.3 | 2285 | 45.7 |
| 15 | 1249 | 25.4 | 1760 | 35.2 |
| 30 | 705 | 14.3 | 1450 | 29.0 |
| 40 | 584 | 11.9 | 850 | 17.0 |
| 50 | 487 | 9.9 | 700 | 14.0 |

TABLE 7

| Bad smell substance | Acetic acid | |
|---|---|---|
| Deodorizer | Example 3 | |
| Time (min) | ppm | Remaining ratio |
| 0 | 4341 | 100% |
| 5 | 1841 | 42.4 |
| 10 | 800 | 18.4 |
| 15 | 345 | 7.9 |
| 30 | 56 | 1.3 |
| 40 | Not detected | — |

We claim:

1. A method of deodorizing comprising applying a colloidal antimony pentoxide as a deodorant to a site or material to be deodorized.

2. The method according to claim 1, wherein the colloidal antimony pentoxide has a particle size of 2 to 200 mμ.

3. The method according to claim 1, wherein the colloidal antimony pentoxide is acidic.

4. The method according to claim 1, wherein a surface of the colloidal antimony pentoxide is modified by a metal compound.

5. The method according to claim 4, wherein the metal compound is at least one compound of a metal selected from the group consisting of metals of I valence, II valence and III valence and of IV valence Ti, Zr and Sn.

6. The method according to claim 5, wherein the metal compound is selected from the group consisting of LiOH, NaOH, KOH, Mg(OH)$_2$, Ca(OH)$_2$, Sr(OH)$_2$, Ba(OH)$_2$, Zn(OH)$_2$, Sn(OH)$_2$, Ni(OH)$_2$, MgO, CaO, SrO, BaO, ZnO, NiO, Li$_2$CO$_3$ Na$_2$CO$_3$, K$_2$CO$_3$, LiCl, NaCl, Li$_2$SO$_4$, Na$_2$SO$_4$, MgCl$_2$, CaCl$_2$, SrCl$_2$, BaCl$_2$, Mg(NO)$_3$, Ca(NO)$_3$, Mg(OH)$_3$.3MgCO$_3$, CaCO$_3$, MgCO$_3$, MgSO$_4$, ZnCl$_2$, ZnSO$_4$, ZnCO$_3$, Pb(OH)$_2$, PbCO$_3$, Pb(NO$_3$)$_2$, Sn(OH)$_2$, SnCl$_2$, FeCl$_2$, FeSO$_4$, NiSO$_4$, CuSO$_4$, CuCl$_2$, AO$_2$(OH)$_5$Cl, Al$_2$SO$_4$, Al(NO$_3$)$_3$, sodium aluminate, Cr(NO)$_3$, BiOCl, KAl(SO$_4$)$_2$.12H$_2$O, SbOCl, ZrOCl$_2$, ZrO(NO$_3$)$_2$, zirconyl carbonate, K$_3$SnO$_3$.3H$_2$O, TiCl$_4$ and SnCl$_4$.

7. The method according to claim 6, wherein the surface-modified colloidal antimony pentoxide is prepared by mixing an acidic antimony pentoxide sol and an aqueous metal compound solution and then drying.

8. The method according to claim 6, wherein the metal compound is added in terms of oxide 0.1 to 40 % by weight based on antimony pentoxide.

9. The method according to claim 1, wherein a surface of the colloidal antimony pentoxide is modified by ammonia or an organic base.

10. The method according to claim 9, wherein the organic base is at least one compound selected from the group consisting of an amine, a quaternary ammonium salt and an amine type surfactant.

11. The method according to claim 10, wherein the organic base is at least one compound selected from the group consisting of monoethanol amine, triethanol amine, N-(β-aminomethyl)ethanolamine, tetraethanolammonium hydroxide, monomethyltriethanolammonium hydroxide, polyoxyethylenedodecylamine, polyoxyethyleneoctadecylamine, polyoxyethylene tallow alkylamine and polyoxyethylene tallow alkylpropylenediamine.

12. The method according to claim 9, wherein the ammonia or the organic base is present in an amount of 0.05 to 50 % by weight based on the antimony pentoxide.

13. The method according to claim 9, wherein the surface-modified colloidal antimony pentoxide is prepared by mixing an acidic antimony pentoxide sol and at least one of ammonia and an organic base and then drying.

14. The method according to claim 4, wherein a surface of the surface-modified colloidal antimony pentoxide as defined in claim 4 is further modified by an acidic substance.

15. The method according to claim 14, wherein the acidic substance is selected from the group consisting of oxalic acid, tartaric acid, citric acid, stearic acid, L-ascorbic acid, alkylbenzenesulfonic acid, paratoluenesulfonic acid, glyoxal, silicic acid, phosphoric acid, metaphosphoric acid, pyrophosphoric acid, sulfuric acid, molybdic acid, tungstic acid and vanadic acid.

16. The method according to claim 14, wherein the acidic substance is present in an amount of 0.05 to 20 % by weight based on the antimony pentoxide.

17. The method according to claim 14, wherein the surface-modified colloidal antimony pentoxide is prepared by mixing an acidic antimony pentoxide sol and an aqueous metal compound solution, drying the mixture, mixing the mixture and an acidic substance and then drying.

18. The method according to claim 9, wherein a surface of the surface-modified colloidal antimony pentoxide as defined in claim 9 is further modified by an acidic substance.

19. The method according to claim 18, wherein the acidic substance is selected from the group consisting of oxalic acid, tartaric acid, citric acid, stearic acid, L-ascorbic acid, alkylbenzenesulfonic acid, paratoluenesulfonic acid, glyoxal, silicic acid, phosphoric acid, metaphosphoric acid, pyrophosphoric acid, sulfuric acid, molybdic acid, tungstic acid and vanadic acid.

20. The method according to claim 18, wherein the acidic substance is present in an amount of 0.05 to 20% by weight based on the antimony pentoxide.

21. The method according to claim 18, wherein the surface-modified face-modified colloidal antimony pentoxide is prepared by mixing an acidic antimony pentoxide sol and at least one of ammonia and an organic base, drying the mixture, mixing the mixture and an acidic substance and then drying.

22. The method according to claim 1, wherein a surface of a surface-modified antimony pentoxide modified by at least one metal compound selected from the group consisting of IV valence Ti, Zr and Sn, is modified by ammonia or an organic base.

23. The method according to claim 22, wherein the organic base is at least one compound selected from the group consisting of an amine, a quaternary ammonium salt and an amine type surfactant.

24. The method according to claim 22, wherein the surface-modified colloidal antimony pentoxide is prepared by mixing an acidic antimony pentoxide sol and at least one metal compound selected from the group consisting of IV valence Ti, Zr and Sn, drying the mixture, mixing the mixture and at least one of ammonia and an organic base and then drying.

25. A deodorizer composition comprising a colloidal antimony pentoxide, wherein a surface of the colloidal antimony pentoxide is modified by ammonia or an organic base.

26. The deodorizer composition according to claim 25, wherein the organic base is at least one compound selected from the group consisting of an amine, a quaternary ammonium salt and an amine type surfactant.

27. The deodorizer composition according to claim 26, wherein the organic base is at least one compound selected from the group consisting of monoethanol amine, triethanol amine, N-(β-aminomethyl)ethanolamine, tetraethanolammonium hydroxide, monomethyltriethanolammonium hydroxide, polyoxyethylenedodecylamine, polyoxyethyleneoctadecylamine, polyoxyethylene tallow alkylamine and polyoxyethylene tallow alkylpropylenediamine.

28. The deodorizer composition according to claim 25, wherein the ammonia or the organic base is present in an amount of 0.05 to 50 % by weight based on the antimony pentoxide.

29. The deodorizer composition according to claim 25, wherein the surface-modified colloidal antimony pentoxide is prepared by mixing an acidic antimony pentoxide sol and at least one of ammonia and an organic base and then drying.

30. The deodorizer composition according to claim 25, wherein the colloidal antimony pentoxide has particle size of 2 to 200 mμ.

31. The deodorizer composition according to claim 25, wherein the colloidal antimony pentoxide is acidic.

32. The deodorizer composition according to claim 25, wherein a surface of the surface-modified colloidal antimony pentoxide is further modified by an acidic substance.

33. The deodorizer composition according to claim 32, wherein the acidic substance is selected from the group consisting of oxalic acid, tartaric acid, citric acid, stearic acid, L-ascorbic acid, alkylbenzenesulfonic acid, paratoluene-sulfonic acid, glyoxal, silicic acid, phosphoric acid, metaphosphoric acid, pyrophosphoric acid, sulfuric acid, molybdic acid, tungstic acid and vanadic acid.

34. The deodorizer composition according to claim 32, wherein the acidic substance is present in an amount of 0.05 to 20 % by weight based o n the antimony pentoxide.

35. The deodorizer composition according to claim 32, wherein the surface-modified colloidal antimony pentoxide is prepared by mixing an acidic antimony pentoxide sol and at least one of ammonia and an organic base, drying the mixture, mixing the mixture and acidic substance and then drying.

36. The deodorizer composition comprising a colloidal antimony pentoxide, wherein a surface of the colloidal antimony pentoxide is modified by a metal compound and wherein a surface of the surface-modified colloidal antimony pentoxide is further modified by an acidic substance.

37. The deodorizer composition according to claim 36, wherein the acidic substance is selected from the group consisting of oxalic acid, tartaric acid, citric acid, stearic acid, L-ascorbic acid, alkylbezenesulfonic acid, paratoluene-sulfonic acid, glyoxal, silicic acid, phosphoric acid, metaphosphoric acid, pyrophosphoric acid, sulfuric acid, molybdic acid, tungstic acid and vanadic acid.

38. The deodorizer composition according to claim 36, wherein the acidic substance is present in an amount of 0.05 to 20 % by weight based on the antimony pentoxide.

39. The deodorizer composition according to claim 36, wherein the surface-modified colloidal antimony pentoxide is prepared by mixing an acidic antimony pentoxide sol and an aqueous metal compound solution, drying the mixture, mixing the mixture and an acidic substance and then drying.

40. The deodorizer composition according to claim 36, wherein the colloidal antimony pentoxide has a particle size of 2 to 200 mμ.

41. The deodorizer composition according to claim 36, wherein the colloidal antimony pentoxide is acidic.

42. The deodorizer composition according to claim 36, wherein the metal compound is at least one compound of a metal selected from the group consisting of metals of I valence, II valence, and III valence and of IV valence Ti, Zr and Sn.

43. The deodorizer composition according to claim 42, wherein the metal compound is selected from the group consisting of $LiOH$, $NaOH$, $KOH$, $Mg(OH)_2$, $Ca(OH)_2$, $Sr(OH)_2$, $Ba(OH)_2$, $Zn(OH)_2$, $Sn(OH)_2$, $Ni(OH)_2$, $MgO$, $CaO$, $SrO$, $BaO$, $ZnO$, $NiO$, $Li_2CO_3$, $Na_2CO_3$, $K_2CO_3$, $LiCl$, $NaCl$, $Li_2SO_4$, $Na_2SO_4$, $MgCl_2$, $CaCl_2$, $SrCl_2$, $BaCl_2$, $Mg(NO_3)_3$, $Ca(NO_3)_3$, $Mg(OH)_3 \cdot 3MgCO_3$, $CaCO_3$, $MgCO_3$, $MgSO_4$, $ZnCl_2$, $ZnSO_4$, $ZnCO_3$, $Pb(OH)_2$, $PbCO_3$, $Pb(NO_3)_2$, $Sn(OH)_2$, $SnCl_2$, $FeCl_2$, $FeSO_4$, $NiSO_4$, $CuSO_4$, $CuCl_2$, $Al_2(OH)_5Cl$, $Al_2SO_4$, $Al(NO_3)_3$, sodium aluminate, $Cr(NO_3)_3$, $BiOCl$, $KAl(SO_4)_2 \cdot 12H_2O$, $SbOCl$, $ZrOCl_2$, $ZrO(NO_3)_2$, zirconyl carbonate, $K_3SnO_3 \cdot 3H_2O$, $TiCl_4$ and $SnCl_4$.

44. The deodorizer composition according to claim 43, wherein the metal compound is added in terms of oxide 0.1 to 40 % by weight based on the antimony pentoxide.

45. A deodorizer composition comprising a colloidal antimony pentoxide, wherein a surface of a surface-modified antimony pentoxide modified by at least one metal compound selected from the group consisting of IV valence Ti, Zr and Sn, is modified by ammonia or an organic base.

46. The deodorizer composition according to claim 45, wherein the organic base is at least one compound selected from the group consisting of an amine, a quaternary ammonium salt and an amine type surfactant.

47. The deodorizer composition according to claim 45, wherein the surface-modified colloidal antimony pentoxide is prepared by mixing an acidic antimony pentoxide sol and at least one metal compound selected from the group consisting of IV valence Ti, Zr and Sn, drying the mixture, mixing the mixture and at least one of ammonia and an organic base and then drying.

48. The deodorizer composition according to claim 45, wherein the colloidal antimony pentoxide has a particle size of 2 to 200 mμ.

49. The deodorizer composition according to claim 45, wherein the colloidal antimony pentoxide is acidic.

* * * * *